United States Patent [19]
Daly et al.

[11] Patent Number: 4,883,661
[45] Date of Patent: Nov. 28, 1989

[54] USE OF ARGININE AS AN LYMPHOKINE SYNERGIST

[76] Inventors: John M. Daly, 559 Ferndale La., Haverford, Pa. 19041; John Reynolds, 4617 Pine St., Apt. H-510, Philadelphia, Pa. 19143

[21] Appl. No.: 107,287

[22] Filed: Oct. 9, 1987

[51] Int. Cl.$^4$ .................. A61K 37/02; A61K 45/02
[52] U.S. Cl. .................. 424/85.2; 424/85.1; 424/85.4; 424/85.5; 424/85.6; 424/85.7; 514/2; 514/8; 514/21; 514/885; 435/811; 530/351
[58] Field of Search ........ 530/351; 424/85, 85.1–85.7; 514/2, 8, 21; 435/811

[56] References Cited

U.S. PATENT DOCUMENTS 4,222,907 9/1980 Katz .................. 424/88

FOREIGN PATENT DOCUMENTS 1209037 8/1986 Canada .

OTHER PUBLICATIONS

Adrian Barbul, "Arginine: Biochemistry, Physiology, and Therapeutic Implications", Journal of Parenteral and Entereal Nutrition 10: 227–238 (1986).
Varner, CA, vol. 92, 1980, #161571b.
Chany et al., CA, vol. 98, #155213u, 1983.
Chany et al, CA, vol. 98, #11168r, 1982.
Brunetti et al, CA, vol. 108(5), 1987, #384361.
Cerutti et al, CA, vol. 103(23), 1985, #189307q.
Varner, et al., "Temporal Serum Concentrations of Growth Hormone, Thyrotropin, Insulin, and Gucagon in Sheep Immunized Against Somatostatin", Endocrinology, vol. 106, No. 3, 1027–1032 (1980).
Cerutti, et al., "Importance of Coordinated Immune Stimulation in Experimental Antitumor Treatment", Int. J. Immunopharmac, vol. 7, No. 5, 783–787 (1985).
Chany, et al., "Antitumor Effect of Arginine Butyrate in Conjunction with Corynebacterium Parvum and Interferon", Int. J. Cancer, vol. 30: 489–493 (1982).

*Primary Examiner*—Garnette D. Draper
*Attorney, Agent, or Firm*—Woodcock, Washburn, Kurtz, MacKiewicz & Norris

[57] ABSTRACT

It has been found that arginine serves to increase the receptivity of cells to lymphokines such as interleukin-2 and interferon. An improved method for treating a mammal with one or more lymphokines is disclosed wherein said improvement comprises administering said one or more lymphokines to said mammal in combination with an amount of arginine effective to increase the receptivity of cells of said mammal to said one or more lymphokines.

9 Claims, No Drawings

USE OF ARGININE AS AN LYMPHOKINE SYNERGIST

BACKGROUND OF THE INVENTION

This invention relates to an improved method of treating a mammal with a lymphokine such as interleukin 2 wherein said improvement comprises administering said lymphokine in combination with an amount of arginine effective to increase the receptivity of cells of said mammal to the lymphokine. Interleukin 2 (IL-2) is a lymphokine which mediates some cytotoxic activity of immune system cells.

Arginine has been known for many years to have pharmacologic properties. Barbul reviewed the uses of arginine in his article, "Arginine: Biochemistry, Physiology, and Therapeutic Implications", J. of Parenteral and Enteral Nutrition, 10: 227–238, 1986.

Arginine plays a role in protein synthesis, biosynthesis of amino acids and derivatives and the urea cycle. All tissues utilize arginine for cytoplasmic and nuclear protein biosynthesis.

During the last 40 years arginine has been classified as semiessential for human nutrition. This classification was given by Rose, who in a series of experiments, studied the dietary essentiality of amino acids from the standpoints of (1) optimal growth and (2) maintenance of positive nitrogen balance. Rose discovered that adult rats did not require dietary arginine by these criteria, but that the young growing rat demonstrated more rapid growth when receiving dietary arginine. It has been confirmed that dietary arginine is necessary for maximal growth and/or nitrogen balance in young dogs, cats, rabbits and pigs. Dietary arginine was found to be dispensable for weight and nitrogen balance maintenance in adult mammals and humans.

Administration of arginine is known to have a protective effect against the effects of ammonia in the bloodstreams of humans and other mammals. In experiments it was found that administration of ammonia to rats induced rapid death due to elevated ammonia levels. However, if arginine was given prior to or concomitantly with the amino acids, glycine or ammonia, the toxic effects of hyperammonemia were abrogated. Urea-cycle related amino acids, such as ornithine and citrulline, share the "detoxifying" effects of arginine, but no other amino acid tested in the acute rat model of ammonia intoxication was found to have this protective activity.

As a result of experimental studies, arginine began to be used clinically in humans with elevated blood ammonia levels (mainly due to liver disease) and the therapeutic effect ranged from excellent to minimal. The clinical use of arginine in hepatic disease has largely been discontinued in the United States and has been replaced by other techniques, especially the use of high branched-chain and low aromatic amino acid mixtures or of some keto analogues of amino acids. Arginine treatment of hepatic diseases remains of interest outside the United States.

Arginine has also been used as an adjunct in the treatment of traumatic wounds. Studies show that arginine is a dietary essential amino acid following injury and that increased uptake of arginine following trauma has beneficial effects by decreasing nitrogen losses and improving the rate of wound healing. Experiments with rats demonstrated that rats given a chemically defined solid amino acid diet lacking arginine fail to grow when subjected to anesthesia and an otherwise mild trauma, i.e. dorsal skin wounding. Weight loss occurred the first day postoperatively and normal weight gain was observed by the second or third day. The addition of 1% arginine HCl to the drinking water 6 days after the injury reversed the weight loss and resulted in 100% recovery, with normal growth and wound healing. Other studies have shown that wound healing in rats is accelerated when arginine is given as a dietary supplement before and/or after wounding. Several of the studies seems to indicate that dietary arginine promotes increased reparative collagen accumulations.

Arginine is also known to have immune effects in humans and mammals. Studies have shown that arginine increases thymic weight in uninjured rats and mice and minimizes the thymic involution that occurs with injury. The gain in thymic weight is due to significant increases in the lymphocyte content of the thymic glands and is accompanied by a significant enhancement in the blastogenesis of the lymphocytes in response to mitogens.

In normal healthy human volunteers, daily oral arginine HCl supplements (30 g) increased peripheral blood lymphocyte blastogenesis in response to concanavalin A and phtyohemagglutin. The effect is evident within 3 days of supplementation and is dependent on in vivo ingestion of arginine; the in vitro incubation of lymphocytes in media containing higher amounts of arginine does not lead to greater blastogenic responses. The exact mechanism of arginine's thymotropic effect is not known.

Another aspect of the immune effects of arginine is its effects on tumor induction and development. Over the past 50 years there have been numerous studies using arginine in a variety of experimental models. (See Barbul, cited above.) In one series of experiments using a solid tumor, the breast adenocarcinoma (C3HBA), arginine slowed tumor appearance as well as reducing tumor incidence in rats. Similar results were obtained in experiments with tumor excision. CBA/J mice were inoculated with C3HBA tumors which were allowed to grow to about 1 cm in diameter. The animals then underwent a gross surgical excision of the tumor. Animals supplemented with arginine after tumor excision showed only a 30% tumor recurrence rate and those mice which subsequently developed tumors had a prolonged survival time. Mice which did not receive supplemental arginine had 100% recurrence of tumors and died.

Anti-tumor immunity is greatly influenced by lymphokines, particularly interleukin-2 (IL-2) and interferon (INF). Lymphokines are the products of activated lymphocytes which exert regulatory effects upon other cells of the immune system. These soluble mediators allow activities such as help, suppression, or cytotoxicity to be manifested by the target cells. Interleukin-2 mediates T cell activation, cytotoxic T lymphocyte development and influences natural killer cell activity.

Arginine has a very low toxicity for normally nourished animals. The $LD_{50}\%$ (intraperitoneal, after 24 hour starvation) for arginine HCl in rats is 18 mM/kg (3.8 g/kg). In human studies, 30 g arginine HCl daily in divided doses for 1 week produced no untoward effects except for mild gastrointestinal discomfort. Patients with renal or hepatic insufficiency may be able to tolerate only smaller dosages.

SUMMARY OF THE INVENTION

This invention provides an improved method for treating a mammal with a lymphokine such as interleukin-2 or interferon wherein said improvement comprises administering said lymphokine in combination with an amount of arginine effective to increase the receptivity of cells of said mammal to the lymphokine. It has surprisingly been found that arginine increased lymphokine receptor activity, such that arginine administered with lymphokines such as IL-2 should increase the cytotoxic effects of the lymphokine. Although the exact mechanism of arginine action is not known, arginine appears to work synergistically with a lymphokine such as IL-2, such that the same level of cytotoxicity can be achieved with smaller amounts of the lymphokine. Since lesser quantities of IL-2 are required to create the desired cytotoxic effects, adverse side effects of IL-2 to the patient should be reduced An object of this invention is therefore to provide an improved method of treating a mammal with one or more lymphokines which method serves to increase the receptivity of cells of said mammal to said one or more lymphokines.

Another object of this invention is the provision of a method of inducing a cytotoxic effect on cells of a mammal by treating said mammal with a lymphokine, said method being effective to increase the receptivity of cells of said mammal to said one or more lymphokines.

Still another object of this invention is the provision of a method of reducing the dosage of lymphokine needed to be administered to induce a cytotoxic effect on treated cells of a mammal.

These and other objects of the present invention will become apparent from the following, more detailed description.

DETAILED DESCRIPTION OF THE INVENTION

Test results have indicated that arginine can increase the receptivity of cells to lymphokines such as interleukin-2 and interferon. The effects of arginine appear to be related to enhanced production or utilization of the lymphokine. The preferred embodiment of this invention utilizes arginine in combination with interleukin-2. The increased receptivity of IL-2 receptors to IL-2 in the presence of arginine was quite unexpected. Although arginine and IL-2 are both known to reduce tumor growth, the combination of arginine and IL-2 should produce cytotoxic effects far beyond those predicted by administration of IL-2 separately. Arginine may in some way prime the cell to either produce more IL-2 receptors or to make the receptors more receptive to IL-2. IL-2 is a very toxic compound, and by enhancing the effects of smaller amounts of IL-2 with arginine, an amino acid with a very low toxicity, side effects of IL-2 action are lessened.

IL-2 or another lymphokine and arginine can be administered in combination in a liquid solution and injected intraperitoneally. The combination can also be administered by supplying arginine in liquid solution for ingestion orally and IL-2 separately in liquid solution for intraperitoneal injection.

EXAMPLE 1

The effect of arginine on IL-2 dependent responses is shown by the following example. The effect of arginine on two IL-2 - dependent responses (T cell activation and cytotoxic T lymphocyte (CTL) development) and on interferon-influenced natural killer (NK) cell activity was evaluated.

CBA/J mice (n=100) received 1% arginine (ARG) dietary supplementation o isonitrogenous glycine (GLY) for al least 10 days. CTL development was determined by sensitizing mice to BALB/C spleen cell alloantigen in vivo ($\times 3$ immunizations) and measuring cytotoxicity against allolymphoblasts as targets. Basal and Poly I:C - induced NK activity was measured against YAC targets. Using indirect immunofluorescence, IL-2 receptor expression (M7/20) on purified splenic T cells was determined 24 and 48 hours after con A activation. Results are presented in Table 1 wherein data are expressed as % toxicity in a 4 hour Chromium release assay (CTL and NK cells only) and % expression (IL-2). (*p,0.05 Student's T test)

TABLE 1

|  | CTK | NK(bas) | NK(Ind) | IL 2 (24 hr) | IL 2 (48 hr) |
|---|---|---|---|---|---|
| ARG | 69 ± 15* | 19 ± 5 | 43 ± 12* | 52 ± 4* | 59 ± 6* |
| GLY | 54 ± 14 | 13 ± 4 | 24 ± 14 | 30 ± 4 | 46 ± 45 |

NK(bas) = NK(basal); NK(Ind) ± NK(Induced)

Supplemental arginine significantly augmented CTL and inducible NK activity and enhanced IL-2 receptor kinetics. These data strongly suggest that the immunomodulatory effects of arginine relate to enhanced production or utilization of lymphokines. IL-2 acts only on cells which have receptors for IL-2.

EXAMPLE 2

The effects of supplemental arginine (ARG) in the malnourished tumor bearing host were evaluated. A/J mice (n=120) received a low protein diet (LPD; 2.5% protein) for 1 week prior to inoculation with C1300 neuroblastoma and were then randomized to receive the LPD alone, the LPD=1% ARG or the LPD=1% glycine (GLY). Body weight, tumor weight and carcass weight were measured weekly and duration of survival was recorded. On day 10, specific T cell cytotoxicity was measured; concanavalin A (con A) stimulation of thymocytes and mixed lymphocyte tumor cell culture (MLTC) were measured on days 14 (d14) and 21(d21) (n=5/group). Data are presented in Table 2.

TABLE 2

|  | ConA+ (d14) | ConA+ (d21) | MLTC+ (d14) | MLTC+ (d21) | Cytotoxicity++ |
|---|---|---|---|---|---|
| ARG | 66.6* ± 12 | 34.8* ± 6 | 4.7* ± 1.5 | 2.2 ± 1.3 | 25* ± 1.5 |
| GLY | 38.4 ± 7 | 24.9 ± 5 | 3.3 ± 0.9 | 2.5 ± 0.8 | 15 ± 1.4 |
| LPD | 32.1 ± 16 | 17.3 ± 7 | 2.9 ± 0.9 | 2.1 ± 1.4 | 13 ± 1.2 |

(d14) = fourteen days; (d21) = twenty-one days
Mean ± SD
*p<0.001
Students t test compared GLY or LPD
+ Stimulation Index: ++ (%), 100:1 Effector to Target ratio (d10)

Both ARG and GLY significantly preserved means total body weight and mean carcass weight compared with LPD mice. ARG significantly ($p<0.05$) retarded tumor growth and prolonged ($p<0.001$) median survival compared with GLY and LPD mice (ARG, 38 days; LPD, 29 days; GLY, 30 days).

Supplemental ARG preserved host nutritional status, retarded tumor growth and augmented immune responses in tumor bearing protein malnourished mice. The effect on immune responses and tumor growth was not due to supplemental nitrogen alone and was specific to ARG. The prolonged survival compared with GLY correlated with augmented tumor recognition (MLTC) and specific toxicity.

What is claimed is:

1. An improved method of treating a mammal with interleukin-2 to increase the receptivity of cells of said mammal to said lymphokine to enhance the cytotoxic effect of said lymphokine on cells of said mammal wherein said improvement comprises administering interleukin-2 to said mammal in combination with an amount of arginine effective to increase the receptivity of cells of said mammal to interleukin-2.

2. A method of inducing a cytotoxic effect on cells of a mammal comprising applying to said mammal an effective amount of interleukin-2 in combination with an amount of arginine effective to increase the receptivity of cells of said mammal to said interleukin-2.

3. A method of reducing the dosage of interleukin-2 needed to be administered to induce a cytotoxic effect on treated cells of a mammal comprising administering to said mammal said interleukin-2 in combination with an amount of arginine effective to increase the receptivity of cells of said treated mammal to said interleukin-2.

4. The method of claim 1 where said interleukin-2 and said arginine are administered in combination in a liquid solution injected intraperitoneally.

5. The method of claim 1 where said interleukin-2 is injected intraperitoneally and said arginine is ingested orally.

6. The method of claim 2 where said interleukin-2 and said arginine are administered in combination in a liquid solution injected intraperitoneally.

7. The method of claim 2 where said interleukin-2 is injected intraperitoneally and said arginine is ingested orally.

8. The method of claim 3 where said interleukin-2 and said arginine are administered in combination in a liquid solution injected intraperitoneally.

9. The method of claim 3 where said interleukin-2 is injected intraperitoneally and said arginine is ingested orally.

* * * * *